(12) United States Patent
Brunnberg et al.

(10) Patent No.: US 8,177,759 B2
(45) Date of Patent: May 15, 2012

(54) MEDICAMENT DELIVERY DEVICE

(75) Inventors: Lennart Brunnberg, Tyresö (SE); Kenny Kai Fung Cheung, Bromma (SE)

(73) Assignee: SHL Group AB, Nacka Strand (SE)

( * ) Notice: Subject to any disclaimer, the term of this patent is extended or adjusted under 35 U.S.C. 154(b) by 0 days.

(21) Appl. No.: 12/996,140

(22) PCT Filed: May 29, 2009

(86) PCT No.: PCT/EP2009/056664
§ 371 (c)(1),
(2), (4) Date: Dec. 10, 2010

(87) PCT Pub. No.: WO2009/147112
PCT Pub. Date: Dec. 10, 2009

(65) Prior Publication Data
US 2011/0082420 A1    Apr. 7, 2011

(30) Foreign Application Priority Data

Jun. 5, 2008 (SE) .................................. 0801327

(51) Int. Cl.
A61M 5/00 (2006.01)
(52) U.S. Cl. .......................... 604/208; 604/209
(58) Field of Classification Search .............. 604/82, 604/191, 208, 209
See application file for complete search history.

(56) References Cited

U.S. PATENT DOCUMENTS

| | | | | |
|---|---|---|---|---|
| 4,973,318 A | * | 11/1990 | Holm et al. | 604/208 |
| 5,514,097 A | * | 5/1996 | Knauer | 604/136 |
| 5,665,066 A | * | 9/1997 | Fischer | 604/82 |
| 6,562,006 B1 | * | 5/2003 | Hjertman et al. | 604/208 |
| 6,893,420 B2 | * | 5/2005 | Arnisolle | 604/135 |
| 7,427,275 B2 | * | 9/2008 | DeRuntz et al. | 604/207 |
| 7,704,237 B2 | * | 4/2010 | Fisher et al. | 604/208 |
| 2007/0142789 A1 | * | 6/2007 | Fisher et al. | 604/207 |
| 2008/0027397 A1 | * | 1/2008 | DeRuntz et al. | 604/220 |
| 2008/0103523 A1 | * | 5/2008 | Chiu et al. | 606/200 |
| 2010/0065049 A1 | * | 3/2010 | Farieta et al. | 128/203.15 |
| 2010/0106085 A1 | * | 4/2010 | Perot | 604/83 |

* cited by examiner

*Primary Examiner* — Jackie Ho
*Assistant Examiner* — Gerald Landry, II
(74) *Attorney, Agent, or Firm* — Potomac Patent Group PLLC

(57) ABSTRACT

A medicament delivery device includes distal and proximal housings; a medicament container having a slidable stopper partially, slidably arranged within the proximal housing; a plunger rod within the distal housing having a proximal end abutting the stopper; a driver within the distal housing operably connected to the plunger rod for driving the plunger rod and stopper toward the device's proximal end; and a priming device having a distal end including an engagement mechanism arranged to cooperate with an engagement mechanism at the housing's proximal end, an end wall abutting the container's proximal end, and a passage on the end wall. An engagement mechanism at the priming device's proximal end cooperates with a delivery member engagement mechanism. Distal displacement of the priming device relative to the proximal housing causes distal displacement of the container relative to the plunger rod, forcing proximal displacement of the stopper, thereby priming the container.

12 Claims, 5 Drawing Sheets

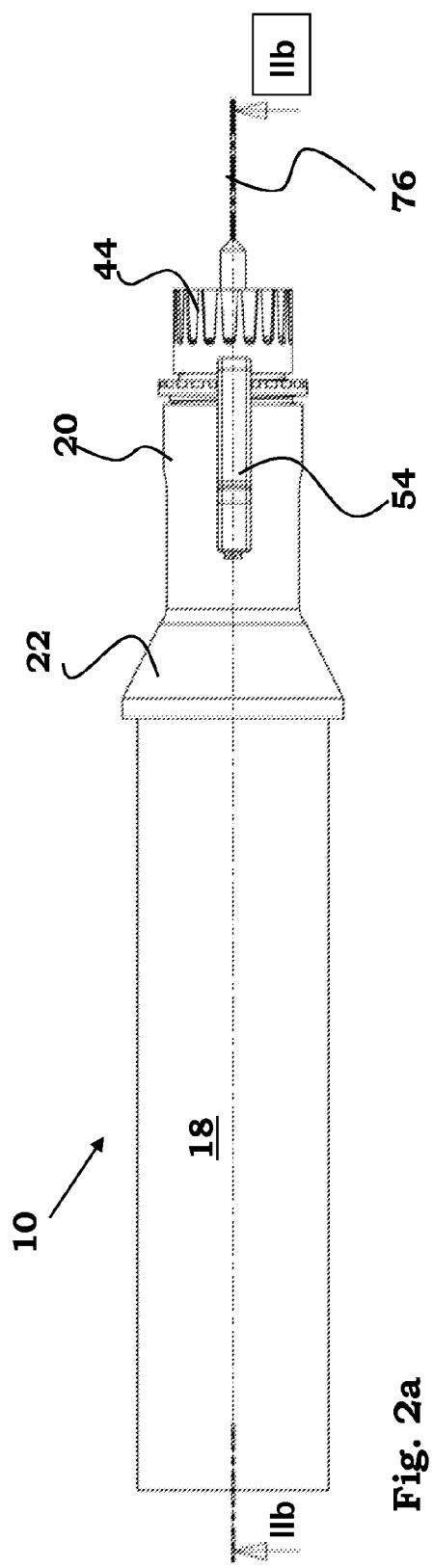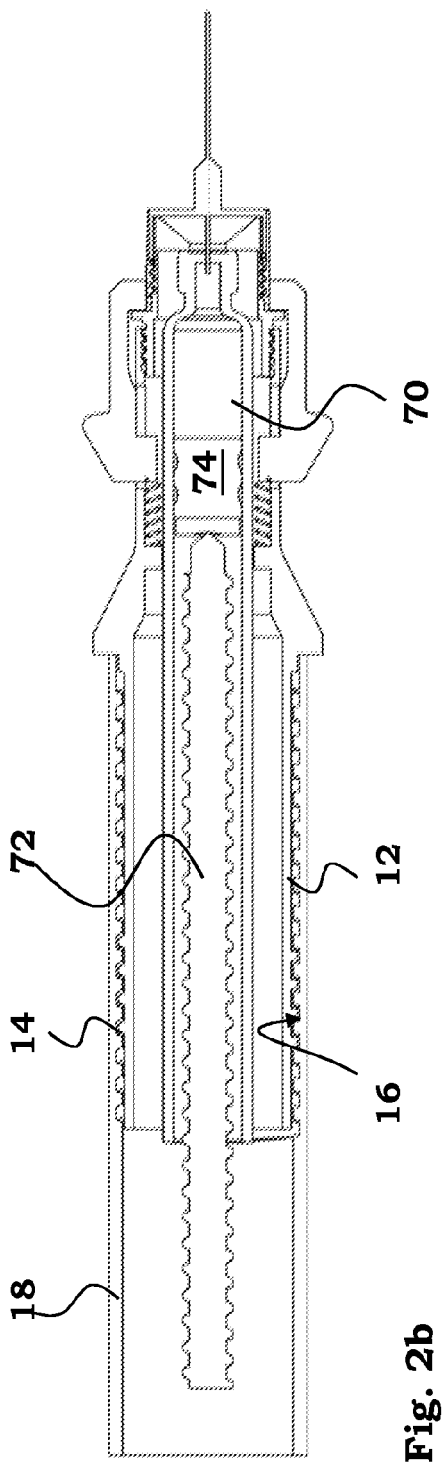
Fig. 2a
Fig. 2b

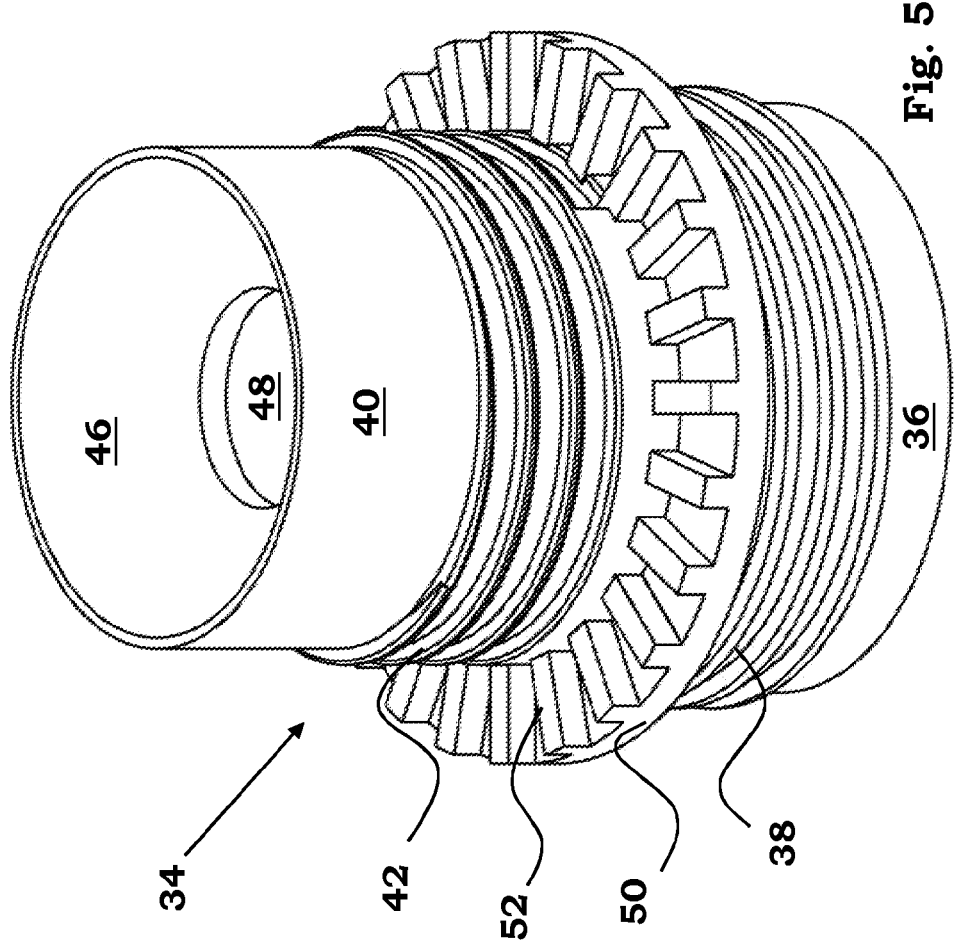
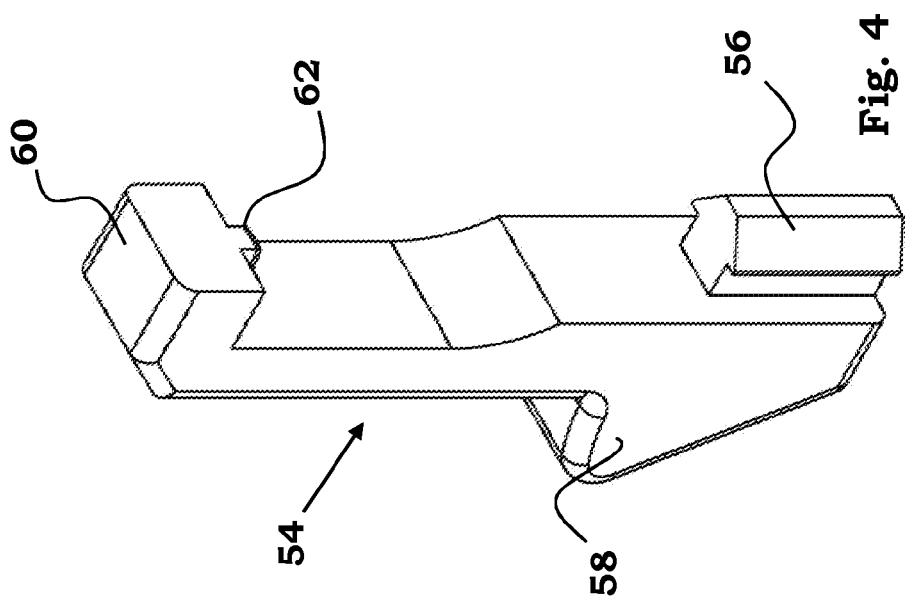

MEDICAMENT DELIVERY DEVICE

TECHNICAL AREA

The present invention relates to a medicament delivery device that must be primed before the administering of a dose of medicament.

BACKGROUND OF THE INVENTION

The development of medical delivery devices has become more and more directed towards the ability for the patient themselves to administer a medicament in an easy, safe and reliable way. For these medical devices, there are generally different types of medicaments that can be stored for a long time and that are packaged in cartridges or the like, containing a ready-to-use medicament in liquid state. There are also other type of medicaments that are a mixture of a medicament agent (e.g. lyophilized, powdered or concentrated liquid) and a diluent (e.g. water, dextrox solution or saline solution), wherein these type of medicaments can not be pre-mixed and stored for a long time because the medicament agent is unstable and can be degraded and loses its effect quickly. Hence, the patients have to perform the mixing within a limited time period prior to the delivery. In order to facilitate the mixing, cartridges or the like comprises at least two chambers, one chamber containing the medicament agent and the other chamber containing the diluent.

Conventionally injection devices are elongated devices with proximal and distal ends. Moreover, said injection devices comprise a cartridge or the like, with one or more chambers containing a medicament to be delivered. Said conventional injection devices are further provided with a plunger rod that is adapted to be in contact with a piston provided inside the cartridge or the like. When a patient or operator wants to administer a dose of medicament, a pointed needle is mounted on the distal end. Upon a force exerted on the piston by the plunger rod, the piston will move forward inside the cartridge to expel the medicament from the cartridge or the like. In many cases, the cartridge contains some quantities of air because it is difficult to obtain a complete filling of medicament.

With a multi-chamber cartridge the medicament agent has to be mixed with the diluent. A multi-chamber cartridge or the like usually contains quite a lot of air, especially when the medicament agent is in powder form, which air is present when the medicament and the diluent are mixed. Further, also the needle contains air in its interior when it is mounted. It is also known that air can be sucked into the cartridge if the patient lets the needle be mounted on the cartridge or the like for a longer period of time and atmospheric conditions change.

This entrapped air is often desirable to get removed before injection. One danger is otherwise that the entrapped air is injected into the patient, which could cause injuries. Another aspect, even if the air would not cause direct harm, is that the first injected dose will be smaller than intended because of the amount of air, hence dose accuracy is reduced. There is further a psychological aspect. A patient may be worried if there is air entrapped and visual in a cartridge of an injector, even though the air may not cause any harm. The mere knowledge that there is air in the cartridge, and that the air might be injected, could be sufficient for a patient not to do want to use the device.

In order to remove the air or gas that is entrapped in the cartridge or the like and/or the needle, priming needs to be performed by means of expelling a small dose of medicament. If at least a droplet or a short liquid jet is not expelled at the sharp point of the needle, another small dose of medicament should often be actuated. In view of that, sometimes the patients desire to set an unnecessary large dose in order to be sure that all air has been expelled. Further, some cartridges have a very small overfill, i.e. the excess quantity of medicament apart from the actual doses. It could also be that the medicament is very expensive. In both cases it is necessary to limit the amount of medicament that is expelled during priming.

Patent document EP 1 365 823 discloses a needle-less injector having a dual chamber medicament cartridge. When a front nozzle portion of the injector is threaded into the injector body, a drug plunger is forced into the medicament cartridge for expelling any air in the medicament cartridge. When the nozzle portion reaches its stop position a drive gas cartridge is activated for forcing medicament through the skin of the patient.

The drawback with this solution is that the plunger of the device has to be manipulated, rendering the construction of the device unnecessarily complicated for the function and purpose, which solution also is very linked to needleless injectors.

The document US 2004/0236285 discloses a medication dispensing apparatus comprising a priming mechanism accessible from the outside of the apparatus in order to prime the medicament container. The priming can be performed whether or not the apparatus is in a loaded state or not. The priming mechanism comprises a drum part that is rotatable manually by a user. The drum can only be rotated in one direction, the priming direction in order to ensure that the user performs the priming correctly. However, the priming mechanism can not be locked in the priming direction, and is readily accessible by any user, whereby there is a pronounced risk that priming operations may be performed intentionally or unintentionally during subsequent injections of doses, whereby the precision and possible a number of doses are lost.

BRIEF DESCRIPTION OF THE INVENTION

The aim of the present invention is to provide a medicament delivery device comprising a priming device which is easy to use, yet safe and reliable.

This aim is obtained by the device characterised by the features of the independent patent claims. Preferable embodiments of the present invention are the subject of the dependent patent claims.

According to a main aspect of the invention, it is characterised by a medicament delivery device comprising a generally tubular distal housing part; a generally tubular proximal housing part releasibly connected to said distal housing part; a medicament container having opposite proximal and distal ends and a slidable stopper, wherein the container is partially and slidably arranged within the proximal housing part; a plunger rod having opposite proximal and distal ends and being arranged within said distal housing, wherein the proximal end of the plunger rod is abutting the stopper of the container; drive means arranged within said distal housing and being operably connected to said plunger rod for driving said plunger rod and thereby said stopper towards the proximal end of the device; characterised in that the device further comprises a priming device having a distal end comprising tune engagement means arranged to cooperate with corresponding tune engagement means arranged at the proximal housing, an end wall abutting the proximal end of the container, a passage arranged on said end wall, and a proximal end comprising delivery member engagement means arranged to cooperate with corresponding delivery member engagement means arranged on a delivery member; wherein the priming device is arranged and designed such that a tune distal displacement of the priming device in relation to the proximal housing part causes a distal displacement of the container in relation to the plunger rod, whereby the plunger rod force the stopper to be proximally displaced and thereby a priming of the container is performed.

According to another aspect of the present invention, said tune engagement means are fine pitch threads.

According to a further aspect of the present invention, said device further comprises at least one priming locking means being releasebly connected to both said priming device and said proximal housing part for locking said priming device to said proximal housing part.

According to yet another aspect of the present invention, said at least one priming locking means comprises an axially slidable locking arm having a locking tooth operably connected to a locking ratchet arranged on said priming device.

According to another aspect of the present invention, said locking ratchet is arranged with teeth having a design such that the priming device is capable to be rotated only in one direction.

According to a further aspect of the present invention, the medicament container is a multiple chamber container comprises at least two substances.

According to one variant of the present invention, the distal housing part comprises mix engagement means arranged to cooperate with corresponding mix engagement means arranged on the distal end of the proximal housing part, such that a distal displacement of the proximal housing part in relation to the distal housing part causes a distal displacement of the container in relation to the plunger rod, whereby the plunger rod forces the stopper to be proximally displaced and thereby a mixing of the substances within the container is performed.

According to another variant of the present invention, said mix engagement means are large pitch threads.

There are a number of advantages with the present invention. The priming device is performed by in a fine tuning displacement action, which enables a very precise movement of the medicament container in relation to the plunger rod. This enables the user to stop the priming operation when eventual air inside the container has been expelled and just when liquid medicament starts to be expelled. This ensures that a minimal amount of medicament is expelled and thus wasted during the priming operation.

Further, the priming device is arranged with priming locking means. This is to prevent, or minimize the risk, that the priming device can be displaced further, or even back, which otherwise either would mean expelling more liquid medicament or loosing the dose precision. The locking also ensures that, if the medicament delivery device is capable of delivering multiple doses, it is not possible to manipulate or prime the device one or more times between doses, which otherwise could mean that one or more doses are lost without the use being aware of it, which ultimately could lead to that the medicament container is empty even if for example a dose counter arranged to the device, indicates that there are doses left.

The priming locking means could be arranged differently depending on desired function and application. The priming locking means could be releasable which means that it is possible to unlock the priming device. This is an advantage for example if the device is a multi-dose device where the device needs to be primed after each delivery member replacement. The injector could also be a multi-usage device, such that and empty container is replaced by a new container, which needs to be primed.

These and other aspects of and advantages with the present invention will become apparent from the following detailed description and from the accompanying drawings.

BRIEF DESCRIPTION OF THE DRAWINGS

In the following detailed description of the invention, reference will be made to the accompanying drawings, of which FIG. 2a shows a side view of the injector of FIG. 1, FIG. 2b shows a cross-sectional view taken along the line IIb-IIb in FIG. 2a, FIG. 3a shows a detailed side view of a component of the injector of FIG. 1, FIG. 5 shows a perspective view of one variant of a priming device comprised in the present invention.

DETAILED DESCRIPTION OF THE INVENTION

In the present application, when the term "distal part/end" is used, this refers to the part/end of the medicament delivery device, or the parts/ends of the members thereof, which under use of the medicament delivery device is located the furthest away from the medicament delivery site of the patient. Correspondingly, when the term "proximal part/end" is used, this refers to the part/end of the medicament delivery device, or the parts/ends of the members thereof, which under use of the device is located closest to the medicament delivery site of the patient.

Figure 1:
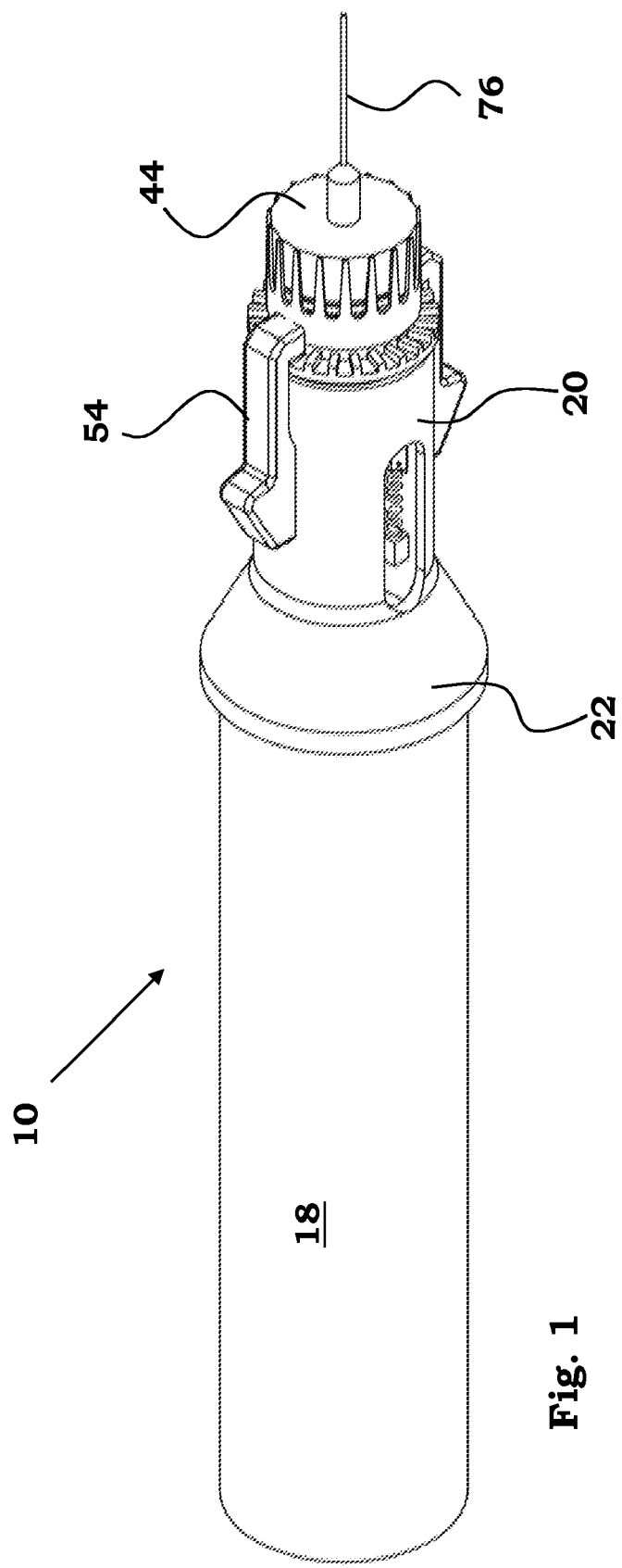
FIG. 1 shows a perspective view of an injector comprising the present invention.
Figure 3A:
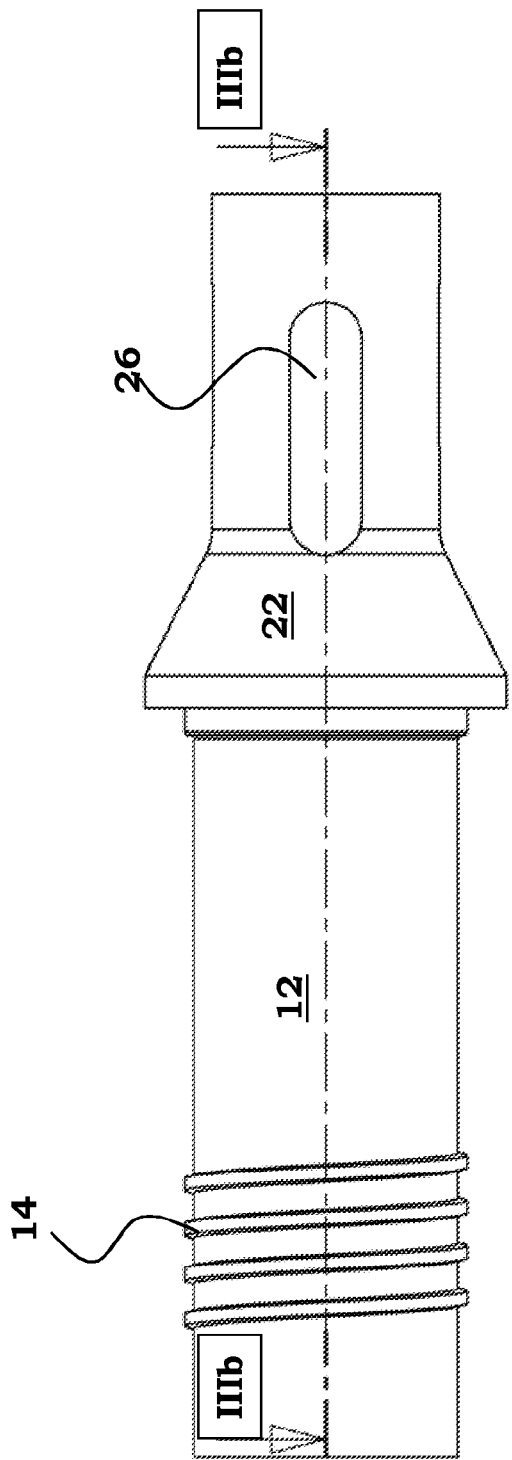
FIG. 3b shows a cross-sectional view taken along the line IIIb-IIIb in FIG. 3a, FIG. 4 shows a perspective view of a holding means comprised in the present invention.
Figure 3B:
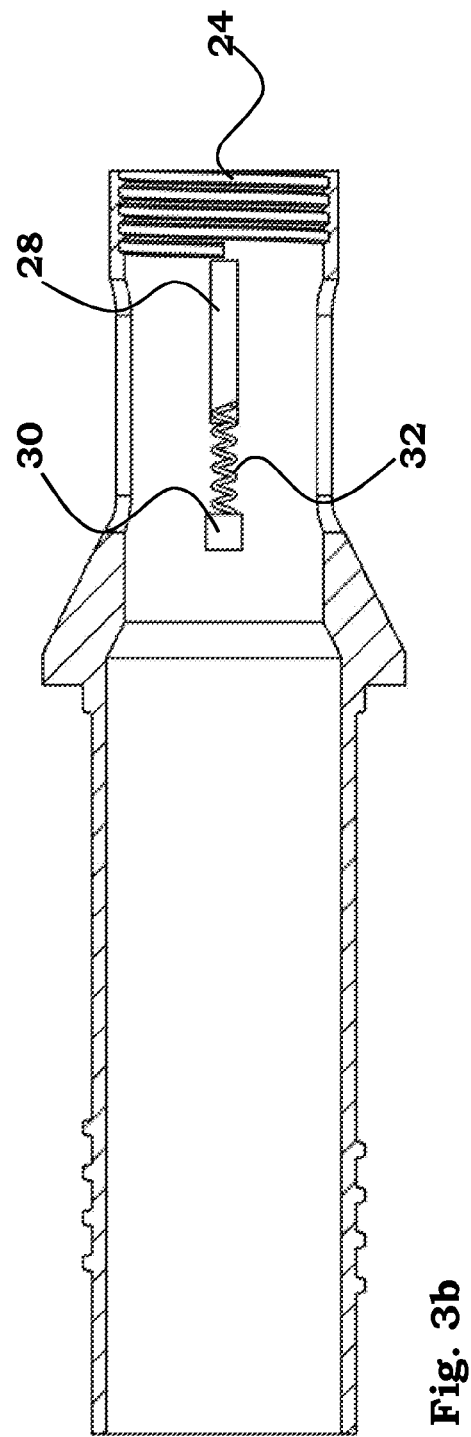

The FIGS. 1 and 2 show a medicament delivery device 10 comprising a generally tubular distal housing part 18; a generally tubular proximal housing part 12 releasibly connected to said distal housing part, a medicament container 70 having opposite proximal and distal ends and a slidable stopper, wherein the container is partially and slidably arranged within the proximal housing part; a plunger rod 72 having opposite proximal and distal ends and being arranged within said distal housing, wherein the proximal end of the plunger rod is abutting the stopper of the container; drive means arranged within said distal housing and being operably connected to said plunger rod for driving said plunger rod and thereby said stopper towards the proximal end of the device; wherein the device further comprises a priming device 34 having a distal end comprising tune engagement means 38 arranged to cooperate with corresponding tune engagement means 24 arranged at the proximal housing, an end wall 46 abutting the proximal end of the container, a passage 48 arranged on said end wall, and a proximal end comprising delivery member engagement means 42 arranged to cooperate with corresponding delivery member engagement means arranged on a delivery member; wherein the priming device 34 is arranged and designed such that a tune distal displacement of the priming device in relation to the proximal housing part causes a distal displacement of the container 70 in relation to the plunger rod 72, whereby the plunger rod force the stopper to be proximally displaced and thereby a priming of the container is performed.

The drive means (not shown) is operably connected to the plunger rod 72 such that the plunger rod is displaced towards the proximal end of the device when said drive means is activated. The drive means may comprises resilient means, first locking means for holding said resilient means in a pre-tensioned state, activation means for releasing said first locking means, and/or second locking means for locking said activation means. The resilient means may be in a pre-tensioned state or alternatively may be pre-tensioned by manually operation means.

The distal end of the proximal housing part 12 is arranged with mix engagement means 14 on its outer circumferential surface. These mix engagement means 14 cooperate with corresponding mix engagement means 16 arranged on the inner circumferential surface at the proximal end of the distal housing part, the function of which will be explained below. The mix engagement means are large pitch threads, wherein the pitch is of e.g. ¼ to 1½ of the diameter of the distal end of the proximal housing part. Further, the proximal end 20 of the proximal housing part 12 is also tubular with a somewhat smaller diameter. A shoulder 22 having a bevelled surface is arranged between the distal end and the proximal end of the proximal housing part.

The proximal end of the proximal housing part 12 is arranged with the tune engagement means 24 on its inner circumferential surface, with at least one window 26 on the side surface, with at least one slit 28 on the side surface nearest the tune engagement means 24, with at least one ledge 30 on its inner circumferential surface, and with at least one resilient means as e.g. a spiral springs 32 attached to the at least one ledge 30. The at least one ledge 30 being distally located on the same longitudinally axis of the at least one slit 28.

The priming device 34 according to the present invention is shown in FIGS. 2 and 5. It comprises a first tubular distal part 36 arranged with the tune engagement means 38 on its outer circumferential surface, which engagement means 38 are arranged to cooperate with the tune engagement means 24 of the proximal housing. It further comprises a second tubular proximal part 40 arranged with delivery member engagement means as e.g. threads 42 on its outer circumferential surface, arranged to cooperate with corresponding delivery member engagement means as e.g. threads of a delivery member as e.g. a needle attachment cap 44, FIG. 1. The second tubular proximal part 40 is arranged with the end wall 46 sloping inwards towards the distal end of the device, where the passage 48 is arranged. The proximal end of the medicament container abuts the distal end surface of the end wall 46. The two tubular parts 30, 40 are divided by a shoulder 50 provided with a locking ratchet 52 on one side surface thereof. The tune engagement means are fine pitch threads, wherein the pitch is of e.g. ⅕ to 1/20 of the diameter of the second tubular proximal part 40 of the priming device.

Further, the device comprises at least one priming locking means 54, as e.g. an arm, being releasebly connected to both said priming device and said proximal housing part for locking said priming device to said proximal housing part. The least one priming locking means is slidably arranged in the at least one slit 28 via a generally T-shaped holder 56, and is forced upwards towards to proximal end by the at least one spring 32. The at least one priming locking means also comprises an axially slidable locking arm 60 having a locking tooth 62 operably connected to a locking ratchet 52 arranged on the shoulder 50 of said priming device, and wherein said slidable locking arm 60 is a radial inwardly extending protrusion on. The at least one priming locking means 54 is further provided with a radial outwardly extending protrusion 58.

The device is intended to function as follows. When the device is delivered to a user/patient, a medicament container is already placed within the proximal housing part 12, the priming device is attached to the proximal housing part, the proximal housing part is attached to the distal housing part, and the proximal end of the plunger rod is abutting the stopper arranged within the medicament container.

When the medicament container is a single chamber medicament container; a delivery member as e.g. a pen needle 76 is attached onto the second tubular proximal part 40 of the priming device 34. In order to prime the container, i.e. removing any air entrapped in the container, the at least one priming locking means 54 is lifted and the priming device 34 is tuned displaced e.g. fine screwed into the front housing 12. This causes the container 70 to be displaced in the distal direction. Because the plunger rod 72 is stationary and is abutting the stopper within the container, it exerts a pressure inside the container, which causes entrapped air to be expelled through the delivery member 76. As soon as any liquid medicament is expelled through the needle, the displacement of the priming device 34 is stopped and the injector is ready for use. The at least one priming locking means is positioned in the at least one slit and pushed towards the distal end of the device against the force of the spring 32 whereby the tooth 62 engages the ratchet 52 of the shoulder 50 of the priming device 34, whereby the latter is prevented from being rotated any further.

Figure 6:
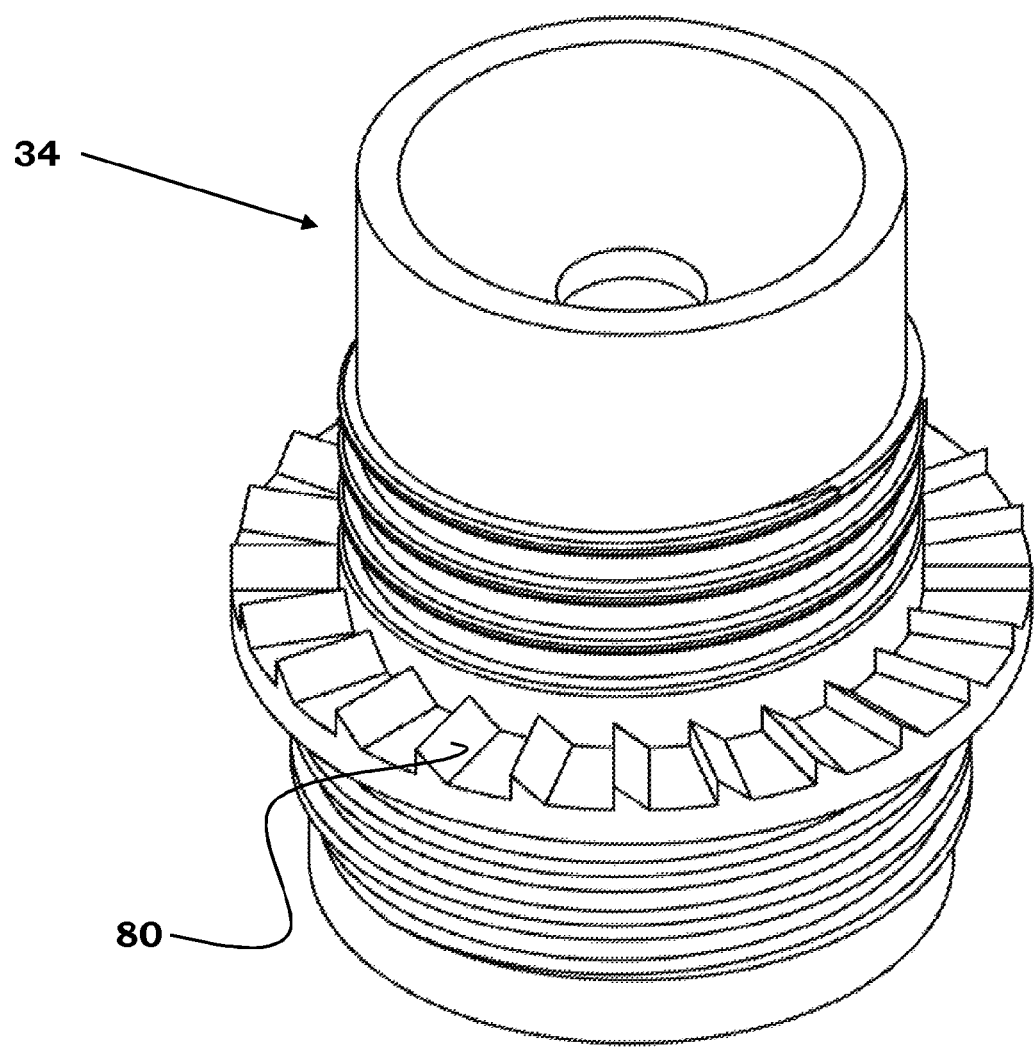
FIG. 6 shows a perspective view of another variant of a priming device comprised in the present invention.

When the medicament container 70, FIG. 2b, comprises at least two separate chambers, one with medicament and one with diluents; the proximal housing part 12 is displaced e.g. threaded into the distal housing part 18. Because the plunger rod 72 is stationary and is abutting the stopper within the container, the stopper 74 of the container is forced against the plunger rod 72, whereby a mixing is obtained. The device is then shaken somewhat in order to complete the mixing. The result is shown in the windows 26 of the proximal housing part. Now a delivery member as e.g. pen needle 76 is attached e.g. threaded onto the second tubular proximal part 40 of the priming device 34. In order to prime the container, i.e. removing any air entrapped in the container, the at least one priming locking means 54 is lifted and the priming device 34 is displaced e.g. screwed into the front housing 12. This causes the container 70 to be displaced in the distal direction. Because the plunger rod 72 is stationary and is abutting the stopper within the container, it exerts a pressure inside the container, which causes entrapped air to be expelled through the delivery member 76. As soon as any liquid medicament is expelled through the needle, the screwing of the priming device 34 is stopped and the injector is ready for use. The at least one priming locking means is positioned in the at least one slit and pushed towards the distal end of the device against the force of the spring 32 whereby the tooth 62 of the at least one priming locking means 54 engages the ratchet 52 of the shoulder 50 of the priming device 34, whereby the latter is prevented from being rotated any further. An alternative is also to have a ratchet 80, FIG. 6, arranged with teeth having bevelled surfaces cooperating with the tooth 62 such that the priming device is capable to be rotated only in one direction and preferably with an audible and tactile click-function.

It is of course possible to attach the delivery member 76 onto the priming device 34 after the priming device is threaded into the proximal end of the proximal housing part.

It is to be understood that device can also be provided without the at least one priming locking means 54 and that when the priming is performed the device must be positioned with the delivery member pointing upwards.

The device now is positioned at the intended delivery site e.g. an injection site, the delivery member being a pen needle 76 penetrates the skin, and the medicament is injected by activating the drive means, either manually or automatically depending on type of device.

The above mentioned priming locking means 54 enables further priming operations because they can be moved out of contact with the priming device. This is an advantage for example if the injector is a multi-dose injector where the device needs to be primed after each needle replacement. The injector could also be a multi-usage injector, such that and empty container is replaced by a new container, which needs to be primed.

It is however to be understood that different types of priming locking means for preventing unintentional rotation of the priming device could be used. For example, a cap or the like that after priming is pushed over the priming device and locks it in position and having locking means of its own, that prevents any further movement of the cap or the priming device. Thereby the priming device is completely locked from being displaced.

It is also to be understood that the mixing step may be performed in many other ways than that described above. For example when the mixing is performed manually, it might be done by merely pushing the proximal end of the priming device against a hard surface, such as a table.

The mixing may also be performed automatically by suitable drive means, capable of pushing the plunger rod forward. Such automatic mixing functions are described in EP 1 814 615 and EP 1 843 808 where spring force means are capable of pushing the plunger forward in order to perform the mixing step upon activation.

It is to be understood that the embodiment described above and shown in the drawings is to be regarded only as a non-limiting example of the invention and that it may be modified in many ways within the scope of the patent claims.

The invention claimed is:

1. A medicament delivery device, comprising:
   a generally tubular distal housing part;
   a generally tubular proximal housing part releasably connected to the distal housing part;
   a medicament container having opposite proximal and distal ends and a slidable stopper, wherein the container is partially and slidably arranged within the proximal housing part;
   a plunger rod having opposite proximal and distal ends and being arranged within the distal housing part, wherein the proximal end of the plunger rod abuts the stopper;
   a drive mechanism arranged within the distal housing part and operably connected to the plunger rod for driving the plunger rod and thereby the stopper toward a proximal end of the device;
   a priming device having a distal end comprising a tune engagement mechanism arranged to cooperate with a corresponding tune engagement mechanism arranged at the proximal housing part, an end wall abutting the proximal end of the container, a passage arranged on the end wall, and a proximal end comprising a delivery member engagement mechanism arranged to cooperate with a corresponding delivery member engagement mechanism arranged on a delivery member; wherein the priming device is arranged such that a tune distal displacement of the priming device in relation to the proximal housing part causes a distal displacement of the container in relation to the plunger rod, whereby the plunger rod forces the stopper to be proximally displaced, thereby priming the container; and
   at least one priming locking device releasably connected to both the priming device and the proximal housing part for locking the priming device to the proximal housing part.

2. The device of claim 1, wherein the tune engagement mechanism includes fine-pitch threads.

3. The device of claim 1, wherein the at least one priming locking device comprises an axially slidable locking arm having a locking tooth operably connected to a locking ratchet arranged on the priming device.

4. The device of claim 3, wherein the locking ratchet includes teeth arranged such that the priming device is rotatable in only one direction.

5. The device of claim 1, wherein the medicament container is a multiple chamber container and includes at least two substances.

6. The device of claim 5, wherein the distal housing part comprises a mix engagement device arranged to cooperate with a corresponding mix engagement device arranged on the distal end of the proximal housing part, such that distal displacement of the proximal housing part in relation to the distal housing part causes distal displacement of the container in relation to the plunger rod, whereby the plunger rod forces the stopper to be proximally displaced, thereby mixing substances within the container.

7. The device of claim 6, wherein the mix engagement devices are large-pitch threads.

8. A medicament delivery device, comprising:
   a generally tubular distal housing part;
   a generally tubular proximal housing part releasably connected to the distal housing part;
   a medicament container having opposite proximal and distal ends and a slidable stopper, wherein the container is partially and slidably arranged within the proximal housing part;
   a plunger rod having opposite proximal and distal ends and being arranged within the distal housing part, wherein the proximal end of the plunger rod abuts the stopper;
   a drive mechanism arranged within the distal housing part and operably connected to the plunger rod for driving the plunger rod and thereby the stopper toward a proximal end of the device;
   a priming device having a distal end comprising a tune engagement mechanism having fine-pitch threads arranged to cooperate with a corresponding tune engagement mechanism having fine-pitch threads arranged at the proximal housing part, an end wall abutting the proximal end of the container, a passage arranged on the end wall, and a proximal end comprising a delivery member engagement mechanism arranged to cooperate with a corresponding delivery member engagement mechanism arranged on a delivery member; wherein the priming device is arranged such that tune distal displacement of the priming device in relation to the proximal housing part causes distal displacement of the container in relation to the plunger rod, whereby the plunger rod forces the stopper to be proximally displaced, thereby priming the container; and
   at least one priming locking device releasably connected to both the priming device and the proximal housing part for locking the priming device to the proximal housing part, wherein the at least one priming locking device comprises an axially slidable locking arm having a locking tooth operably connected to a locking ratchet arranged on the priming device.

9. The device of claim 8, wherein the locking ratchet includes teeth arranged such that the priming device is rotatable in only one direction.

10. The device of claim 8, wherein the medicament container is a multiple chamber container and includes at least two substances.

11. The device of claim 10, wherein the distal housing part comprises a mix engagement device arranged to cooperate with a corresponding mix engagement device arranged on the distal end of the proximal housing part, such that distal displacement of the proximal housing part in relation to the distal housing part causes distal displacement of the container in relation to the plunger rod, whereby the plunger rod forces the stopper to be proximally displaced, thereby mixing substances within the container.

12. The device of claim 10, wherein the mix engagement devices are large-pitch threads.

* * * * *